United States Patent [19]

Politi et al.

[11] Patent Number: 5,075,329
[45] Date of Patent: Dec. 24, 1991

[54] USE OF 3-INDOLEPYRUVIC ACID AS A PHARMACEUTICAL AGENT FOR THE INHIBITION OF PERIPHERAL DEGENERATIVE PATHOLOGIES

[75] Inventors: Vincenzo Politi; Giovanni DiStazio; Giovanna DeLuca; Mario Materazzi, all of Rome, Italy

[73] Assignee: Polifarma, S.p.A., Rome, Italy

[21] Appl. No.: 394,861

[22] Filed: Aug. 17, 1989

[30] Foreign Application Priority Data

Sep. 29, 1988 [IT] Italy ................................ 48398 A/88

[51] Int. Cl.⁵ .......................................... A61K 31/405
[52] U.S. Cl. .................................................... 514/415
[58] Field of Search ........................................ 514/415

[56] References Cited

FOREIGN PATENT DOCUMENTS

| 0106813 | 4/1984 | European Pat. Off. |
| 0179428 | 10/1985 | European Pat. Off. ............ 514/415 |
| 5120560 | 3/1979 | Japan ................................... 514/415 |
| 8700169 | 1/1987 | PCT Int'l Appl. |
| 8809789 | 12/1988 | PCT Int'l Appl. |

OTHER PUBLICATIONS

Chem Abst. 111:23387f (1989), De Luca et al.
Free Radicals in Medicine and Biology, 10/79.
Free Radicals in Molecular Biology, Aging, and Disease, vol. 27.
The Importance of Free Radicals and Catalytic Metal Ions in Human Diseases, 1985.

*Primary Examiner*—Frederick E. Waddell
*Assistant Examiner*—Zohreh A. Fay
*Attorney, Agent, or Firm*—Birch, Stewart, Kolasch & Birch

[57] ABSTRACT

Indolepyruvic acid shows an inhibitory activity with respect to the degenerative action by oxygen free radical which are responsible for a number of pathologic conditions in various peripheral tissues. The compound can find application in miocardiopathies, inflammations, circulatory shock, arteriosclerosis, and cardiac ischemia.

5 Claims, No Drawings

USE OF 3-INDOLEPYRUVIC ACID AS A PHARMACEUTICAL AGENT FOR THE INHIBITION OF PERIPHERAL DEGENERATIVE PATHOLOGIES

BACKGROUND OF THE INVENTION

1. Field of the Invention

The present invention relates to use of 3-indolepyruvic acid as an agent for blocking the toxic effects of oxygen free radicals by removing them from the environment. The compound can consequently be administered with advantage in the treatment of a number of degenerative diseases originated by oxygen free radicals.

With the term peripheral pathologic conditions, we mean the conditions which are found out of the central nervous system.

2. Description of the Prior Art 3-indolepyruvic acid is a per se well known compound.

A number of methods for its production have been proposed.

In European patent 0106813 a process is described for the enzymatic synthesis of 3-indolepyruvic acid, in which aspartate aminotransferase is used as an enzyme.

In International patent application W087/00169 a process is described for the chemical synthesis of 3-indolepyruvic acid, in which a coupling reaction is used starting from 1-tryptophane.

In International application W088/09789 3-indolepyruvic acid and derivatives thereof have been described as pharmaceutical agents for the treatment of diseases of the central nervous system due to an excess of excitatory aminoacids.

Since several years it has been known that the oxygen free radicals when produced in the organism to an extent higher than the detoxication capability with which living beings are provided, are likely to attack basic cell structures, such as nucleic acids, proteins and membranes, leading at last to the death of the cell, and thus to degenerative diseases of all types in the affected tissues. In the papers of an international Symposium held at Uppsala (Sweden) in 1979, published in Acta Physiol. Scand. Sub 492, the oxygen free radicals were indicated as the cause of a plurality of diseases, both central (cerebral ischemia, hypoglycemia, hypoxiemia) and peripheral (tumours, acute and chronic inflammations, immunological disorders).

In a volume issued by Ravenpress in 1984 ("Free radicals in Molecular Biology, Aging and Disease"), an excess presence of oxygen free radicals is considered as the cause not only of the above mentioned disorders, but also of the normal aging in which all human beings are involved.

In a wide and documented review of 1985 ("The importance of free radicals and catalytic metal ions in human diseases"), published on Molec. Aspects Med. Vol. VIII, pages 89–193, B. Halliwell and M. C. Gutteridge describe the free radicals as the cause of diseases which range from inflammatory and autoimmune disorders to the syndrome from respiratory insufficiency, aging, intestinal and cardiac ischemia, cerebral ischemia including a plurality of neurologic disorders, malaria and tumours.

In the above mentioned international application W088/09789 is described a possible mechanism of transformation of 3-indolepyruvic acid into kynurenic acid, through opening of the indole ring, presumably due to an intervention of oxygen free radicals.

SUMMARY OF THE INVENTION

It has how been surprisingly found that 3-indolepyruvic acid is a powerful inhibitor of the toxic effect due to oxygen free radicals and it can therefore be advantageously used in all the pathologic conditions due to a presence of an excessive amount of free radicals in the organism.

In view of the above, an object of the present invention is the use of 3-indolepyruvic acid as a pharmaceutical agent for curing a peripheral degenerative pathologic condition due to or enhanced by an excess of oxygen free radicals in a peripheral tissue of a patient and more generally of mammals.

Among these pathologic conditions, those cardiocirculatory disorders are particularly indicated which intervene at a muscle level, such as cardiac ischemia, myocardiac disturbances, arteriosclerosis, circulatory shock and inflammations and moreover respiratory diseases, the cause of which is due to an action of oxygen free radicals.

EXPERIMENTAL TESTS

1. EVALUATION OF ANTI-RADICAL ACTIVITY OF 3-INDOLEPYRUVIC ACID (IPA) BY THE MALONDIALDEHYDE (MDA) METHOD

The most commonly used method for evaluating the production of oxygen free radicals in tissues or biological fluids, is the test of production of malondialdehyde (MDA) as described, as an example, in "Methods in Enzymology", Vol. 105 (1984). Briefly this method is based on the fact that the unsaturated fatty acids, which are basic constituents of the biologic membranes, are attacked by oxygen free radicals which break the carbon chain in several points so as to produce MDA as a final product.

The aldehyde is then detected by a simple colorimetric method using a reactant containing thiobarbituric acid.

The method of evaluation of the product MDA, in the presence and in the absence of IPA, has been used in three different experimental tests:

(a) EVALUATION OF THE ACTIVITY OF RADICALS IN "IN VITRO" SYSTEMS

This test serves the purpose of putting into evidence a direct action by IPA ion the capture of free radicals present in a solution, with the consequent exclusion of an action by other metabolites which can be formed by IPA in biologic fluids.

The production of radicals was activated by a system comprising iron ascorbate ions and phosphatidylcholine, the most usual constituent of the biological membranes.

| Results: | |
|---|---|
| IPA dose | MDA inhibition % |
| $5 \times 10^{-6}$M | 10 |
| $1 \times 10^{-5}$M | 35 |
| $2 \times 10^{-5}$M | 65 |

The results show that IPA is able "in vitro" to block the degrading action of oxygen on the unsaturated fatty acids present in the biologic membranes. Moreover it is also shown that the action is dose-dependent.

(b) EVALUATION OF THE RADICAL ACTIVITY IN LUNG HOMOGENATE

This test serves the purpose of testing whether IPA is able to block a degradation of the biological membranes due to free radicals, in the lung tissue also, in which is present a high concentration of enzymes which degrade the membrane phospholipids.

| Results: | |
|---|---|
| IPA dose | MDA inhibition % |
| $5 \times 10^{-6}M$ | 8 |
| $1 \times 10^{-5}M$ | 32 |
| $2 \times 10^{-5}M$ | 70 |

Again in this situation it has been shown that IPA is able to antagonize in a dose-dependent manner the degradation of membrane phospholipids due to free radicals.

(c) EVALUATION OF THE RADICAL ACTIVITY IN BRAIN HOMOGENATE

As neuron cells are the most rich in biological membrane and consequently they are more likely to be subjected to a destructive attack by the free radicals, IPA was also tested on brain homogenate, stimulated with the conventional system of iron ascorbate ions for the production of free radicals. The results are as follows:

| Results: | |
|---|---|
| IPA dose | MDA inhibition % |
| $1 \times 10^{-6}M$ | 10 |
| $5 \times 10^{-6}M$ | 18 |
| $1 \times 10^{-5}M$ | 42 |
| $2 \times 10^{-5}M$ | 78 |
| $1 \times 10^{-4}M$ | 100 |

The results are in agreement with those obtained in the preceding tests, and they show that IPA is a very good agent inhibiting damage produced by free radicals on biological membranes.

In conclusion, IPA has shown itself to be able to powerfully antagonize the chain reactions of radicals which are activated by oxygen free radicals on the biological membranes. As far as efficiency is concerned, IPA can be favourably compared to the best known antioxidant agents in the above tests.

The tests of capture of free radicals have been extended for the purpose of evaluating whether the effect was of general extent, or whether it is restricted to an effect on the biological membranes.

(2) EVALUATION OF THE ANTIRADICAL ACTIVITY OF IPA BY DPPH TEST

Compound DPPH (diphenyl-picryl-hydrazyl) is a stabilized free radical which remains unchanged in ethanol for relatively long times. The compounds which act as "radical scavengers" can be tested by following the decrease in optical density at the spectrophotometer (517 nm) after addition to the solution containing DPPH.

IPA has shown itself to be an excellent free radical scavenger, in that a considerable decrease in the optical density can be observed (40% in 30 minutes) when the compound was added at a dose of $10^{-6} M$.

(3) EVALUATION OF THE ANTIRADICAL ACTIVITY OF IPA BY THE CHEMILUMINESCENCE METHOD

Chemiluminescence is a method of detection which in recent years has gained an increasing importance for the determination of various compounds of a short half-life. It appears of particular advantage for the determination of the oxygen free radicals, in that these produce a partial chemiluminescence which can be enhanced by luminol (see Biochem. Biophys. Res. Communic. 150, 30-44, 1988). By this method it results much easier to test the antiradical effect of a compound, by virtue of a decreased emission of light which is recorded by adequate instrumentation (luminographs).

Using as a source of free radicals the system $Fe^{++}$/hydrogen peroxide, IPA has shown to inhibit the chemiluminescence emitted by luminol in the following percentages:

| IPA concentration | % Inhibition |
|---|---|
| $2.5 \times 10^{-8}M$ | 0 |
| $1.0 \times 10^{-7}M$ | 70 |
| $2.5 \times 10^{-6}M$ | 100 |

These results show that the antiradical action of IPA is furthermore enhanced when phospholipids are not present in the solution. Moreover, it is confirmed that this compound has a power to be compared to the most important antioxidants known to date (see above mentioned Bioch. Biophys. . . . ,).

(4) CARDIAC EFFECTS OF IPA

In order to evaluate whether the antiradical action of IPA can obtain pharmacologic results at the cardiac level, a pattern has been used which enables the sensibility of a muscle to stimulation by catecholamines to be evaluated. In fact, as it has been ascertained that the main damage to the heart occurs in the phase of riperfusion after an acute ischemic attack, and it is known that this damage is due to a release of oxygen free radicals (see for example "Oxygen Radicals in the patholophysiology of heart disease", Kluwer Acad. Publ., 1988, pages 111-122), the present treatment aims to reduce the cardiac stimulation by catecholemines (for example by means of beta-blockants) to avoid a higher damage which occurs when the ischemic tissue is subjected to a metabolic stress.

The experimental pattern involves a preventive denervation of the animals to avoid compensatory effects due to cerebral catecholemines and a measurement of the action of compounds selectively acting on alpha and beta adrenergic receptors present on the cardiac muscle, both in control animals and in animals treated with IPA.

The test was carried out on CD strain rats (225-250 g) aged 12 weeks. The animals were divided into two groups: the first one (control) was treated by N-methyl-glucamine, namely the solvent, at a dose of 5 ml/kG/die for seven days; the second group was treated with IPA at a dose of 100 mg/Kg/die for seven days. On the test day the animals were anaesthetized and spinalized according to the method of Yamaguchi and Kopin (J. Pharmacol. Exptl. Ther. 214, 275-81, 1980). The agonists of catecholemines were injected through a catheter inserted into the carotid. The number of heartbeats per minute was then measured.

The results obtained are resumed in the following tables.

TABLE 1

| Basal values (beats/min.) before and after spinalization | | |
|---|---|---|
| | Before | After |
| Controls | 340 ± 20 | 242 ± 17 |
| Treated | 335 ± 15 | 235 ± 12 |

Each point represents the average of five tests.

TABLE 2

| Reactivity to tyramine (general stimulant) | | |
|---|---|---|
| | % beat/min. increase | |
| | Controls | Treated |
| Tyramine 125 ng/Kg | 11.1 ± 1.8 | 2.7 ± 0.9 * |
| Tyramine 250 ng/Kg | 14.8 ± 2.3 | 3.1 ± 0.7 * |
| Tyramine 500 ng/Kg | 17.9 ± 1.4 | 11.5 ± 1.6 * |

Each point represents the average of 5 tests.
* $p < 0.001$ versus controls.

TABLE 3

| Reactivity to Noradrenaline (alfa- and beta-stimulant) | | |
|---|---|---|
| | % beat/min. increase | |
| | Controls | Treated |
| Noradrenaline 60 ng/Kg | 6.1 ± 1.3 | 1.1 ± 0.9 * |
| Noradrenaline 120 ng/Kg | 10.4 ± 1.4 | 1.3 ± 0.2 * |
| Noradrenaline 250 ng/Kg | 22.3 ± 1.1 | 1.6 ± 1.1 * |

Each point represents the average of 5 tests.
* $p < 0,001$ versus controls.

TABLE 4

| Reactivity to phenylephrine (alfa- stimulant) | | |
|---|---|---|
| | % beat/min. increase | |
| | Controls | Treated |
| Phenylephrine 2.5 mcg/Kg | 12.3 ± 1.5 | 1.5 ± 0.2 * |
| Phenylephrine 5 mcg/Kg | 17.6 ± 1.2 | 1.2 ± 0.4 * |
| Phenylephrine 10 mcg/Kg | 25.3 ± 1.1 | 1.1 ± 0.9 |

Each point represents the average of 5 tests.
* $p < 0.001$ versus controls.

TABLE 5

| Reactivity to isoproterenol (beta-stimulant) | | |
|---|---|---|
| | % beat/min. increase | |
| | Controls | Treated |
| Isoproterenol 2.5 mcg/Kg | 24.4 ± 3.9 | 10.5 ± 2.8 |
| Isoproterenol 5 mcg/Kg | 45.3 ± 6.2 | 21.3 ± 4.6 |

Each point represents the average of 5 tests.
* $p < 0.001$ versus controls.

The results of all tests show that a subacute treatment with IPA significantly reduces the tachicardizing response in the spinalized animals, with all the adrenergic agonists used. This means that IPA produces a protective effect on the cardiac muscle subjected to the action of catecholemines.

(5) ACTIVITY OF IPA IN EXPERIMENTAL SHOCK

A further very serious pathology is circulatory shock. This can be discharged by various pathologic situations, such as a haemorrhage (haemorrhagic shock), an attack by bacterial toxins (endotoxic shock), a decreased systol pressure due to a myocardial infarct (cardiogenic shock), or the presence of extended burned areas on the surface of the body (ustion shock).

As described in some text books (see for example "Cardiovascular Pharmacology", Raven Press, 1984, pages 535–578), the shock always produces a pressure fall at the haemodynamic level, with a consequent redistribution of the blood flow towards the peripheral tissues. Consequently some organs are found with such a deficiency of supply with blood, that they cannot maintain a correct aerobic metabolism. This situation makes the production of oxygen free radicals easier, as shown by the microscopic examination of cells subjected to a severe shock, which die by swelling after the membranes have been disrupted by the action of the radicals.

As a test method, the shock from occlusion of the splanchnic arteries (SAO) was used. In this classic method, an occlusion of the splanchnic artery is produced in the rat after binding of the celiac and mesenteric arteries, thus inducing a gradual decrease of the arterial pressure. After 45 minutes the arteries are suddenly reopened and this produces a vertical fall of pressure with death after five hours.

The action of IPA has been evaluated both after acute administration (100 mg/Kg/os) and after repeated administration (100/Kg/os for seven days). The control animals on the contrary received only N-methylglucamine, namely the solvent used for IPA.

The results are referred in the following table (each value represents the average of 6 animals).

| Treatment | Survival (minutes) |
|---|---|
| Acute N-methylglucamine | 175 ± 2.5 |
| Chronic N-methylglucamine | 169 ± 3.1 |
| Acute IPA | 169 ± 4.2 |
| Chronic IPA | 279 ± 3.5 |

Although the above are only preliminary data and whereas only a rough parameter such as survival has been tested, the above results show that IPA can find application also to reduce damage due to circulatory shock.

(6) ANTIINFLAMMATORY ACTIVITY

The antiinflammatory activity of IPA has been tested by following the conventional system of preliminary screening through carrageenan edema, as described for example in "Screening Methods in Pharmacology", Academic Press, 1965.

Briefly, carrageenan, an irritant agent, is injected into the paw of a rat. This originates an inflammatory reaction, at all times mediated by free radicals and evidenced by a local edema, which is measured by a particular instrument: the so-called mercury platismograph.

Three groups of CD rats (10 animals per group) were treated with N-methylglucamine (controls) or with IPA (50 and 200 mg/Kg), one hour before carrageenan injection. The size of the edema was measured every hour for four hours after injection.

The results are as follows:

| Reduction of edema with respect to controls | | | | |
|---|---|---|---|---|
| | 1 hour | 2 hours | 3 hours | 4 hours |
| IPA 50 mg/Kg | 0 | 14.4% | 32.6% * | 37.7% ** |
| IPA 200 mg/Kg | 0 | 23.9% | 28.7% * | 36.8% ** |

* $p < 0.05$ versus controls
* $p < 0.01$ versus controls

The results show that IPA shows protective effects also on an edema induced by carrageenan, involving a production of oxygen free radicals.

Resuming all the results thus obtained, IPA has shown a powerful antagonistic effect on free radicals, both those coming from oxygen, and those deriving from membrane phospholipids or other chemical species.

As a consequence, IPA can be used as a therapeutical means to withstand all the pathologic situations which are caused or promoted by free radicals.

Among these situations the following can be indicated: cardiac ischemia, arteriosclerosis, circulatory shock, miocardiopathies from Adriamicine and derivatives thereof, inflammations, respiratory diseases, cell aging.

The administration can be effected by pharmaceutical compositions containing the active substance in a dose ranging from 2 to 20 mg/Kg body weight in an administration "per se" or rectal, and in a dose ranging from 1 to 10 mg/Kg body weight in a parenteral administration.

For an oral, parenteral or rectal administration, the usual pharmaceutical forms can be used, such as pills, capsules, solutions, suspensions, injections, suppositories, in association with pharmaceutically acceptable carriers or diluents and excipients.

We claim:

1. A method of treating cardiac ischemia due to or enhanced by an excess of oxygen free radicals which comprises administering to a mammal in need thereof a therapeutically effective amount of 3-indolepyruvic acid.

2. A method of treating myocardiopathies due to or enhanced by an excess of oxygen free radicals which comprises administering to a mammal in need thereof a therapeutically effective amount of 3-indolepyruvic acid.

3. A method of treating an arteriosclerotic disease due to or enhanced by an excess of oxygen free radicals which comprises administering to a mammal in need thereof, a therapeutically effective amount of 3-indolepyruvic acid.

4. A method of treating circulatory shock due to or enhanced by an excess of oxygen free radicals which comprises administering to a mammal in need thereof, a therapeutically effective amount of 3-indolepyruvic acid.

5. A method of treating a muscular inflammatory disorder due to or enhanced by an excess of oxygen free radicals which comprises administering to a mammal in need thereof, a therapeutically effective amount of 3-indolepyruvic acid.

* * * * *